United States Patent
Franzolin

(10) Patent No.: US 9,188,521 B2
(45) Date of Patent: Nov. 17, 2015

(54) METHOD FOR CONTROLLING THE CONCENTRATION OF A COMPONENT OF A GASEOUS MIXTURE RECIRCULATED IN A COOKING CHAMBER, PARTICULARLY IN FOOD COOKING OVENS

(75) Inventor: Enrico Franzolin, Vigodarzere (IT)

(73) Assignee: UNOX S.P.A., Vigodarzere (IT)

(*) Notice: Subject to any disclaimer, the term of this patent is extended or adjusted under 35 U.S.C. 154(b) by 1281 days.

(21) Appl. No.: 13/049,501

(22) Filed: Mar. 16, 2011

(65) Prior Publication Data

US 2011/0232624 A1    Sep. 29, 2011

(30) Foreign Application Priority Data

Mar. 23, 2010    (IT) .............................. PD2010A0093

(51) Int. Cl.
*A21B 1/00*    (2006.01)
*G01N 7/00*    (2006.01)
*G01N 9/36*    (2006.01)

(52) U.S. Cl.
CPC ... *G01N 9/36* (2013.01); *G01N 7/00* (2013.01)

(58) Field of Classification Search
USPC ........... 126/21 R, 369; 236/44 A, 44 R, 44 B, 236/44 C; 318/432, 461, 483, 812–817; 322/29; 388/929–930; 73/24.04, 29.01; 99/469
See application file for complete search history.

(56) References Cited

U.S. PATENT DOCUMENTS

| | | | | |
|---|---|---|---|---|
| 2,676,292 | A * | 4/1954 | Spencer | 318/815 |
| 4,281,288 | A * | 7/1981 | Izumi | 324/76.11 |
| 6,662,628 | B2 * | 12/2003 | Horvath et al. | 73/29.01 |
| 6,938,459 | B2 | 9/2005 | Gruhbaum et al. | |
| 2010/0301034 | A1 * | 12/2010 | Greenwood et al. | 219/400 |

* cited by examiner

*Primary Examiner* — Avinash Savani
*Assistant Examiner* — Vivek Shirsat
(74) *Attorney, Agent, or Firm* — Volpe and Koenig, P.C.

(57) ABSTRACT

A method is provided for controlling a gaseous component concentration of a gaseous mixture, which is recirculated by a ventilator in an oven, which is supplied with power at a predetermined mains frequency and voltage, the ventilator being driven by an asynchronous electric motor of known synchronism speed, the mixture being subjected to a known pressure. The method includes: detecting the temperature of the mixture in the cooking chamber, varying the motor's power supply voltage in order to maintain the motor's rotation speed at a predetermined value, measuring the difference between the mains voltage that supplies the motor and the motor's power supply voltage at the predetermined speed, using the voltage difference, the temperature and the known pressure to determine the component concentration in the mixture, comparing the component concentration which is found with a desired concentration value and, adjusting the component concentration in the cooking chamber.

9 Claims, 1 Drawing Sheet

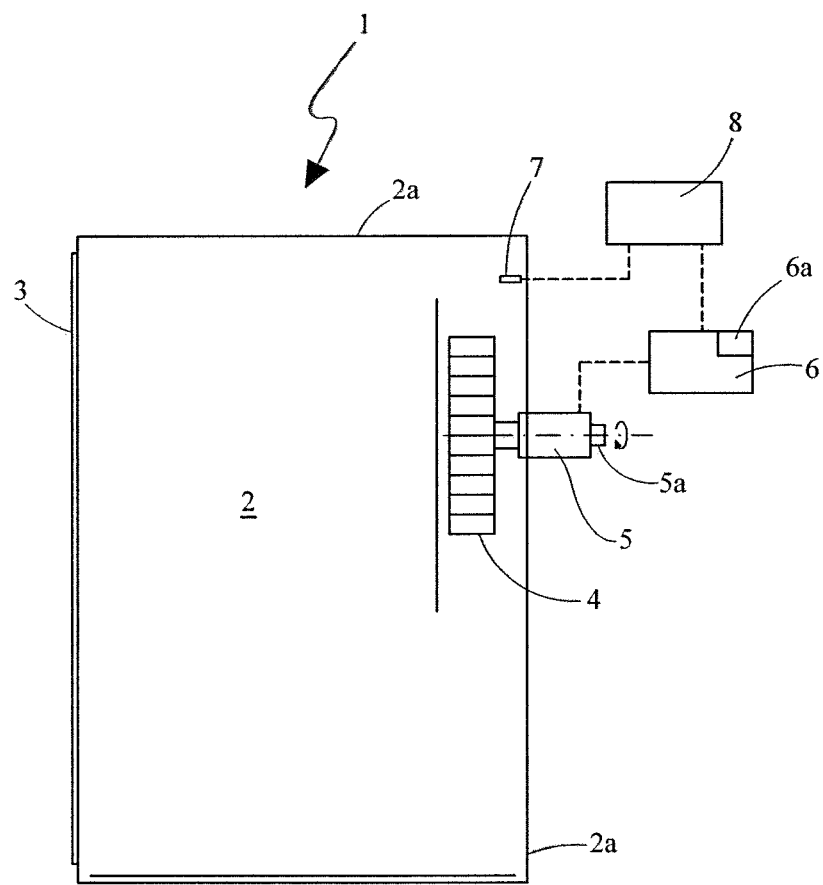

METHOD FOR CONTROLLING THE CONCENTRATION OF A COMPONENT OF A GASEOUS MIXTURE RECIRCULATED IN A COOKING CHAMBER, PARTICULARLY IN FOOD COOKING OVENS

FIELD OF INVENTION

The present invention concerns a method for controlling the concentration of a component of a gaseous mixture in a cooking chamber for food cooking ovens.

BACKGROUND

In the relevant technical field, it is known to provide for the measurement of some parameters correlated to the cooking processes in order to control said processes within the cooking chamber of an oven. Among these parameters are the temperature of the chamber, the pressure, and the concentration of water vapor, which are normally significant for the desired cooking process. For the measurement of the concentration of water vapor it is known to use sensors inserted into the cooking chamber and which utilize the correlation between said parameter and other measurable parameters. For example, sensors are known which utilize the pressure differential measurable between the input and the output of the blading of the fan disposed inside the cooking chamber. Since the pressure differential is correlated to the density of the air which varies from dry air to 100% water vapor, it is possible to measure the percentage of vapor present. Another example is provided by devices for measuring the oxygen present in the mass of air inside the oven, by means of probes suitably calibrated for such measurements.

A principal limitation in the use of sensor means for sensing the vapor concentration inside the cooking chamber lies in the temperature conditions obtainable in the cooking processes which may compromise the functioning thereof or even prevent their use. These sensors are arranged to function in environments with maximum temperatures well below the maximum temperatures which can be reached within the chamber. In addition, the presence of cooking fats inside the chamber renders measurement by means of such sensors difficult and not very reliable.

Another method for controlling the concentration of water vapor within the cooking chamber is known from U.S. Pat. No. 6,662,628. The method described therein provides for correlating the slipping of an asynchronous motor, which drives in rotation ventilation means for the air inside the cooking chamber, to the concentration of water vapor. The variation of the resistant load on the motor due to the density of the air which varies according to the concentration of vapor contained therein and to the temperature, effects a variation in the speed of the motor which can be correlated to the slipping understood as the difference between the speed of synchronism of the asynchronous motor and the speed assumed by the motor as a result of the resistant load.

This variation is in general dependent on the characteristics of the motor, the fan, the voltage and frequency of the power supply, the temperature and also the concentration of water vapor, and in the majority of cases is either too great or too small with respect to the speed which is ideal and desirable for cooking, all this rendering the application of the method not very reliable and precise from the point of view of controlling the vapor concentration in order to achieve a better cooking quality.

SUMMARY

The principal aim of the invention is that of providing a method for controlling the proportion of a component of a gaseous mixture within the cooking chambers of ovens for cooking foods, designed so as to make it possible to remedy the limitations mentioned with reference to the prior art cited.

This aim is achieved by the invention by means of a control method produced in accordance with the appended claims.

BRIEF DESCRIPTION OF THE DRAWING

Further features and advantages of the invention will become clear from the following detailed description of a preferred exemplary embodiment thereof, illustrated by way of non-limiting example with reference to the single appended drawing, which shows a schematic view of a cooking oven arranged for the application of the method according to the invention.

With reference to the drawing cited, a method for controlling the concentration of water vapor according to the invention is applicable to a cooking oven for foods, designated by 1 and only illustrated schematically in the drawing.

DETAILED DESCRIPTION OF THE PREFERRED EMBODIMENTS

The oven 1 is provided with a cooking chamber 2 inside which can receive the foods to be cooked. Said chamber is delimited by walls 2a defining an opening of the oven which can be closed by means of a door 3 for access to the chamber for the introduction and extraction of the foods being cooked.

The oven is provided with heat-generating means, not shown, for example including electrical resistances or a heat exchanger connected to a combustible gas burner. In order to effect the recirculation of air inside the cooking chamber, a fan 4 is also provided, driven in rotation by an electric motor 5, and arranged inside the cooking chamber, the function of which is to induce a forced circulation of air suitable for ensuring the thermal exchange by convection which is suitable for the pre-selected cooking process. Water vapor generators or reducers (which are not shown) are also provided, for example by conveying water inside the cooking chamber in order to increase the concentration of water vapor suitable for the cooking process or by introducing ambient air inside the cooking chamber in order to reduce the concentration thereof.

The oven is supplied with power at the predetermined mains frequency and voltage, respectively indicated by $F_r$ and $V_r$.

The motor 5 is selected as an asynchronous motor, therefore having a known speed of synchronism, and is provided with a device for supplying electric power for the motor, indicated by 6 and illustrated only schematically, with which it is possible to supply power to the motor at a supply voltage V in order to obtain a predetermined rotation speed, as will become clear hereinafter. In the device there is provided a meter 6a for measuring the voltage V or magnitudes correlated thereto (for example the phase cut) and a motor rotation speed meter (tachometer) 5a.

The reference 7 indicates a temperature sensor for detecting the temperature inside the cooking chamber.

When the cooking chamber is open to the outside, atmospheric pressure tends to prevail therein, said pressure depending substantially on the altitude at which the oven is located, and therefore to be regarded as known or in any case determinable. Alternatively, it is possible to provide, if appropriate, a pressure sensor disposed inside the cooking chamber.

The reference 8 indicates overall a data processing apparatus, such as a computer or a microprocessor control center, in which the data detected by the aforesaid sensors are processed and by suitable algorithms there are obtained, at the output, the values of the parameters necessary for controlling the concentration C of water vapor in the cooking chamber with the method described in detail hereinafter.

In the following description, reference will be made to air as the gaseous mixture and to the methods for controlling the concentration of water vapor, as a component of the mixture, present in the air inside the chamber.

The method according to the invention is based on the concept that the rotation speed of the fan (and therefore of the motor), which interacts with the gaseous mixture recirculated inside the cooking chamber, can be assumed to be a function of the geometry of the oven, of the characteristics of the motor, the pressure, the temperature, the voltage and the frequency of the power supply to the motor, as well as the concentration of water vapor. By reason of the diverse density of the air, which varies with the percentage of water vapor present therein and the temperature, the resistant load on the fan varies in correlation, on the basis of the aforesaid parameters.

In a first exemplary embodiment of the method, provision is made first of all for obtaining curves which place the voltage V in relation with the temperature T and the concentration C of vapor at constant frequency and constant pressure as well as for a predetermined speed value.

According to the method, firstly, the temperature T' of the air inside the chamber is detected. The supply voltage V for the motor is then varied (at constant frequency e.g. equal to that of the mains supply) in order to maintain the rotation speed n of the motor at a predetermined value n'. The measurement of the difference between the mains voltage Vr, at which the motor is supplied with power, and the voltage V' at which the motor rotates at the speed n' then takes place. This difference (Vr–V'), the temperature T' and the known pressure (e.g. atmospheric pressure) depend on the concentration C' of the water vapor in the air mixture. If, for example, a state of substantially dry air is created inside the chamber, values for voltage V', temperature T', and speed n' will be obtained which correspond to a vapor concentration C' substantially equal to 0%. If, for example, a state of air substantially saturated with vapor is created in the chamber, the values V", T' and n" corresponding to a concentration C" of vapor equal to 100% are obtained.

In order to determine the values between 0% and 100% it is possible to proceed with techniques of interpolation between the aforesaid extreme values, linear or otherwise, or intermediate states between 0% and 100% of water vapor concentration are created, and the above is repeated.

With such a method it is therefore possible to obtain, as the temperature T varies, sequences of values or diagrams (obtained by predetermined interpolations) in which the supply voltage V for the motor is a function correlated to the temperature T of the chamber at a predetermined speed n of the motor 5, these values being correlated to a certain concentration C of water vapor present in the chamber.

These diagrams may then be used to evaluate, in a specific operative state of the oven, while it is functioning, the value of the concentration of water vapor, in order to compare it with desired values and consequently adjust the concentration of vapor inside the chamber on the basis of the comparison obtained.

In this step it is possible, knowing the supply voltage at a predetermined speed of the motor, and the temperature T of the chamber, to evaluate, using the aforesaid diagrams, the value of the vapor concentration C with which to proceed with controlling same according to a desired value. This sequence of calculating operations is implemented with a suitable algorithm in a program contained in the data processing unit 8, in which are stored the sequences or the diagrams obtained previously and the desired values for vapor concentration together with the other parameters (temperature, time and speed) of the preselected cooking processes.

The method may also provide for the sequence of steps described above, repeated as the temperature T varies, maintaining, for example, the speed n of the motor constant (and equal to a predetermined value), this mode of operation giving preference to the constancy of the speed of the motor and therefore of the fan, which may represent the most suitable choice for certain cooking processes.

Alternatively, provision may be made for the sequence of steps of the method to be repeated as the temperature T varies, varying in addition the speed n of the motor, and preferably as the temperature T increases the predetermined value of the speed n of the fan is increased. A linear proportionality between temperature T and speed n may represent one of the possible choices. With this mode of operation, preference is instead given to the constancy of the thermal exchange as the temperature increases, a choice which may be more suitable for other predetermined cooking processes.

It should be noted that the measurement of the voltage difference (Vr–V') for a certain predetermined speed n' of the motor may be obtained by means of measurement of the phase cut with which the motor 5 is supplied with power (at a speed below the speed of synchronism), utilizing the correlation between voltage and phase cut.

In addition, when a choice is made to vary the power supply voltage V for the motor, it is to be understood that the frequency F remains constant, for example equal to that supplied by the mains network. In this case, the power supply voltage for the motor may be varied, as an alternative to or in combination with the phase cut, by supplying with power one or more electrical resistances (not shown) placed in series with the motor windings. As an alternative to or in combination with the phase cut and the additional electrical resistances, provision may also be made to supply power to the motor with the output voltage of a transformer (or autotransformer) at one or more outputs. The speed regulating device 6 may in addition be designed with a combination of one or more of the aforesaid modes of operation provided for varying the power supply voltage for the motor, at constant frequency.

It is also possible to arrange to vary the frequency F of the motor 5 in order to maintain the speed n thereof at a predetermined value, as taught by the method of the invention. For example, provision may be made for the device 6 to comprise an inverter in order to obtain an output frequency F which is variable, at constant voltage V, with which to supply power to the motor. Provision may also be made for the inverter to supply a voltage and an output frequency which are both variable. In the latter case the predetermined speed of the motor will be obtained by supplying the motor with power at a frequency and voltage which are variable at the output from an inverter device.

The method for controlling the vapor concentration according to the invention thus achieves the aims proposed, providing numerous advantages compared with known solutions.

One advantage is linked to the fact that owing to the method of the invention the limitations which are encountered in the use of known humidity sensors to be placed inside the cooking chamber are remedied, which limitations are due to the high temperatures reached in the cooking process, which may comprise the functioning or prevent the use thereof.

Another advantage is that the method claimed makes it possible to evaluate the vapor concentration and consequently adjust it and ensure that the desired values are maintained, especially the rotation speed, taking into account the course of the variations of the cooking parameters which occur normally in the cooking processes, thus improving the final quality obtainable from such processes.

What is claimed is:

1. A method for controlling the concentration of a gaseous component of a gaseous mixture, said mixture being recirculated by a ventilator in a cooking chamber of an oven, for cooking foods in said chamber, said oven being supplied with power at a predetermined mains frequency and voltage, said ventilator being driven by an asynchronous electric motor of known speed of synchronism, said gaseous mixture being subjected in said chamber to a known pressure, the method comprising:
   detecting a temperature of the gaseous mixture in the cooking chamber,
   varying the voltage of the power supply of the motor in order to maintain the rotation speed of the motor at a predetermined value,
   measuring of the difference between the mains voltage at which the motor is supplied with power and the voltage at which the motor rotates at the predetermined speed,
   using said voltage difference, said temperature and said known pressure to determine the concentration of said component in the mixture,
   comparing the concentration of the component which is found with a desired concentration value and,
   adjusting the concentration of said component in the cooking chamber on the basis of the comparison carried out,
   wherein the predetermined speed of the motor is obtained by phase-cutting of the power supply voltage of the motor, at constant frequency.

2. The method according to claim 1, wherein said component is water vapor and said gaseous mixture is air.

3. The method according to claim 1, wherein said measurement of the voltage difference is obtained via measurement of the phase cut, on the basis of the correlation existing between voltage and phase cut.

4. The method according to claim 1, wherein the predetermined speed of the motor is obtained by supplying with power one or more electrical resistances placed in series with the motor windings, at constant frequency.

5. The method according to claim 1, wherein the predetermined speed of the motor is obtained by supplying power to said motor with the output voltage of a transformer with one or more outputs, at constant frequency.

6. The method according to claim 1, wherein the predetermined speed of the motor is obtained by at least two of the following: by phase-cutting of the power supply voltage of the motor at constant frequency; by supplying with power one or more electrical resistances placed in series with the motor windings at constant frequency; or by supplying power to said motor with the output voltage of a transformer with one or more outputs at constant frequency.

7. The method according to claim 1, wherein the predetermined value of the speed of the motor is kept constant as the temperature varies.

8. The method according to claim 1, wherein the predetermined value of the speed of the motor varies as the temperature varies.

9. The method according to claim 1, wherein the predetermined value of the speed increases as the temperature increases.

* * * * *